(12) United States Patent
Ross

(10) Patent No.: US 9,744,006 B2
(45) Date of Patent: Aug. 29, 2017

(54) ORAL APPARATUSES AND METHODS FOR MANDIBULAR JAW MANIPULATION

(71) Applicant: Gregory K. Ross, LakeLand, MN (US)

(72) Inventor: Gregory K. Ross, LakeLand, MN (US)

(*) Notice: Subject to any disclaimer, the term of this patent is extended or adjusted under 35 U.S.C. 154(b) by 1 day.

(21) Appl. No.: 14/819,856

(22) Filed: Aug. 6, 2015

(65) Prior Publication Data

US 2017/0035533 A1 Feb. 9, 2017

(51) Int. Cl.
| | |
|---|---|
| *A61C 7/36* | (2006.01) |
| *A61F 5/56* | (2006.01) |
| *A61C 7/08* | (2006.01) |
| *A61C 9/00* | (2006.01) |

(52) U.S. Cl.
CPC ............... *A61C 7/36* (2013.01); *A61C 7/08* (2013.01); *A61C 9/004* (2013.01); *A61F 5/566* (2013.01)

(58) Field of Classification Search
CPC .... A61C 7/36; A61C 7/08; A61C 7/00; A61C 7/06; A61F 5/566; A61F 5/56; A61F 2005/563
USPC ................ 433/18–19; 128/859–862
See application file for complete search history.

(56) References Cited

U.S. PATENT DOCUMENTS

| | | | | |
|---|---|---|---|---|
| 5,443,384 A * | 8/1995 | Franseen | ............... | A61C 7/36 433/18 |
| 5,683,244 A * | 11/1997 | Truax | ............... | A61C 7/00 433/24 |
| 6,074,207 A | 6/2000 | Coats | | |
| 6,530,375 B1 * | 3/2003 | Cieslik, Jr. | ............... | A61F 5/566 128/848 |
| 6,604,527 B1 * | 8/2003 | Palmisano | ............... | A61C 7/08 128/848 |
| 6,790,036 B2 | 9/2004 | Graham | | |
| 7,104,790 B2 | 9/2006 | Cronauer | | |
| 7,146,982 B2 | 12/2006 | Mousselon et al. | | |
| 8,192,196 B2 | 6/2012 | Singh | | |

(Continued)

FOREIGN PATENT DOCUMENTS

WO WO 2015103084 A1 * 7/2015 ............. A61F 5/566

OTHER PUBLICATIONS

Ihatecpap.com. Online. I Hate CPAP!, LLC, Online on or before Jul. 17, 2015. Retrieved from the Internet: Oct. 29, 2015. <URL: http://www.ihatecpap.com/oral_appliance.html>.

*Primary Examiner* — Nicholas Lucchesi
*Assistant Examiner* — Shannel Wright
(74) *Attorney, Agent, or Firm* — Bradley C. Fach; Steven R. Kick; PatentFile, LLC

(57) ABSTRACT

An oral apparatus for mandibular jaw manipulation which in some embodiments may include: an upper tray configured to receive a plurality of maxillary teeth and which may have a first upper anchor member coupled to a first side of the upper tray and a second upper anchor member coupled to a second side of the upper tray; a lower tray configured to receive a plurality of mandibular teeth and which may have a first lower anchor member coupled to a first side of the lower tray and a second lower anchor member coupled to a second side of the lower tray. The first upper anchor member may be configured to contact the first lower anchor member and the second upper anchor member may be configured to contact the second lower anchor member to adjust the positional relationship between the mandible and the maxilla of a mouth.

4 Claims, 8 Drawing Sheets

(56) References Cited

U.S. PATENT DOCUMENTS

| | | |
|---|---|---|
| 8,215,312 B2* | 7/2012 | Garabadian ............. A61F 5/566 |
| | | 128/846 |
| 8,459,989 B2 | 6/2013 | Keski-Nisula et al. |
| 2003/0207224 A1* | 11/2003 | Lotte ........................ A61C 7/36 |
| | | 433/6 |
| 2006/0234179 A1 | 10/2006 | Wen et al. |
| 2007/0283967 A1* | 12/2007 | Bailey ..................... A61F 5/566 |
| | | 128/848 |
| 2011/0005526 A1* | 1/2011 | Garabadian ............. A61F 5/566 |
| | | 128/848 |
| 2011/0005527 A1* | 1/2011 | Andrew ................... A61C 7/08 |
| | | 128/848 |
| 2011/0259345 A1* | 10/2011 | Cullen .................... A61F 5/566 |
| | | 128/848 |
| 2013/0239978 A1* | 9/2013 | Stubbs .................. A61C 7/006 |
| | | 128/861 |
| 2013/0323664 A1 | 12/2013 | Parker |
| 2015/0238280 A1* | 8/2015 | Wu ........................ A61C 7/002 |
| | | 433/6 |

* cited by examiner

ORAL APPARATUSES AND METHODS FOR MANDIBULAR JAW MANIPULATION

FIELD OF THE INVENTION

This patent specification relates to the field of orthodontics and dentistry including dental sleep medicine. More specifically, this patent specification relates to systems and methods that alter the maxillary and mandibular dental relationship of a user.

BACKGROUND

The relationship between the mandible and maxilla can have a wide range of consequences. This relationship can affect chewing, biting, facial alignment, and even a person's propensity to snore. A Class II dental relationship is defined as the maxillary arch teeth protruding anteriorly, or mesially of the mandibular teeth. A Class III dental relationship is defined as the mandibular arch teeth protruding anteriorly, or mesially of the maxillary teeth.

These relationships are frequently corrected using orthodontic elastics, headgear, or intra-oral bite correctors (Functional Appliances) that extend between the maxillary and mandibular dental sets. However, orthodontic elastics require frequent replacement. Headgear is often found to be uncomfortable to the wearer and also has a decreased rate of compliance. Intra-oral bite correctors tend to be bulky and uncomfortable to the wearer. Additionally, these types of apparatuses are generally very noticeable, and therefore considered fairly unaesthetic.

Therefore, a need exists for novel oral apparatuses and methods that are able to alter or direct the relationship between the mandible and maxilla in an orthodontic manner. There also exists a need for novel oral apparatuses and methods that are able to alter the positional relationship between the mandible and maxilla to decrease snoring or be used in oral appliance therapy for Obstructive Sleep Apnea. There is a further need for novel oral apparatuses and methods that are able to alter the relationship between the mandible and maxilla for Class II dental relationship or Class III dental relationship correction treatment objectives. Finally, there exists a need for novel oral apparatuses and methods that are able to alter the relationship between the mandible and maxilla in an aesthetic and comfortable manner.

BRIEF SUMMARY OF THE INVENTION

An oral apparatus which is able to adjust or direct the positional relationship between the mandible and maxilla is provided. In some embodiments, the apparatus may comprise: an upper tray configured to receive a plurality of maxillary teeth and which may have a first upper anchor member coupled to a first side of the upper tray and a second upper anchor member coupled to a second side of the upper tray; a lower tray configured to receive a plurality of mandibular teeth and which may have a first lower anchor member coupled to a first side of the lower tray and a second lower anchor member coupled to a second side of the lower tray. The first upper anchor member may be configured to contact the first lower anchor member and the second upper anchor member may be configured to contact the second lower anchor member to adjust the positional relationship between the mandible and the maxilla of a mouth.

In further embodiments, the first and second upper anchor members may be positioned proximate to the maxillary molar teeth and may be configured to contact with the first and second lower anchor members positioned proximate to the mandibular molar teeth to cause the mandible to move forwards relative to the maxilla when the mouth is in a closed position.

In further embodiments, the first and second upper anchor members may comprise an upper contact surface and an upper bite plane and the first and second lower anchor members may comprise a lower contact surface and a lower bite plane.

In still further embodiments, the upper contact surface of the first and second upper anchor members may be configured to contact the lower contact surface of the first and second lower anchor members while the mouth is in a closed position.

According to another embodiment consistent with the principles of the invention, a method of forming an oral apparatus for mandibular jaw manipulation is provided. The method may include the steps of: positioning the lower jaw relative to the upper jaw in a therapeutic bite pattern; recording a digital scan of the upper and lower jaw positioning; positioning anchor members within the digital scan; converting the digital scan to a three dimensional model comprising anchor members on each jaw; and fabricating an oral apparatus using the three dimensional model.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Figure 1:
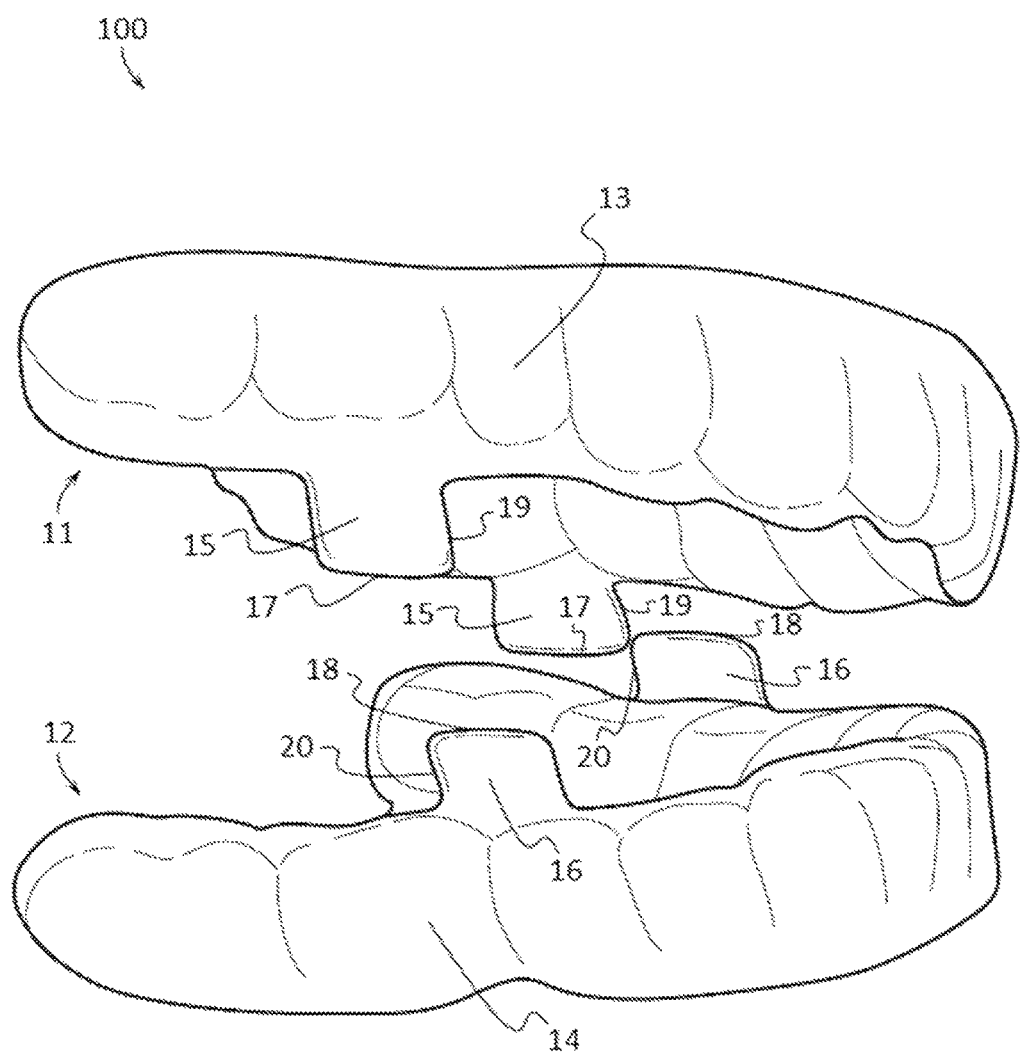
FIG. 1 depicts a side perspective view of an example of an oral apparatus according to various embodiments described herein.
Figure 2:
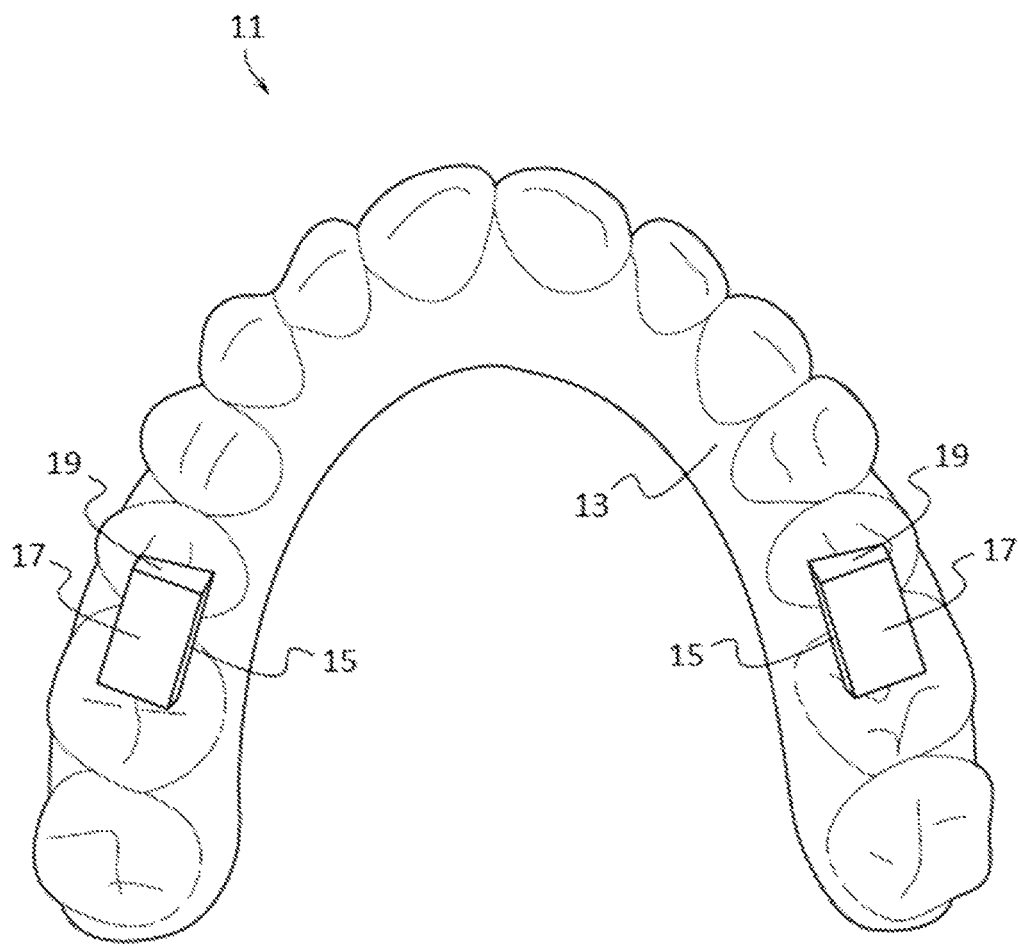
FIG. 2 illustrates a top plan view of an example of an upper element of an oral apparatus according to various embodiments described herein.
Figure 3:
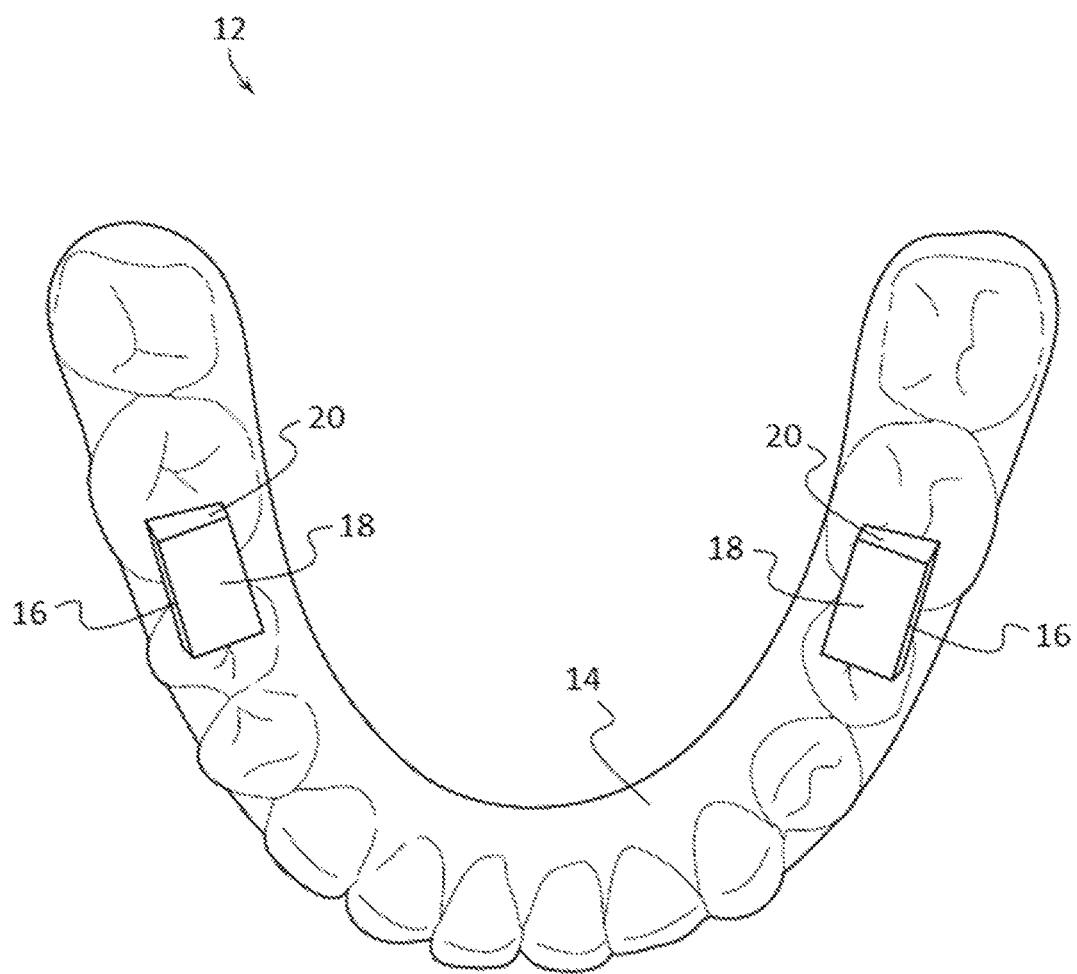
FIG. 3 shows a top plan view of an example of a lower element of an oral apparatus according to various embodiments described herein.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

To clarify the description of the invention certain dental terms should be understood. Upper and lower teeth are termed maxillary and mandibular teeth, respectively.

Front teeth are anterior teeth and back teeth are posterior teeth. Anterior teeth are incisors and are named centrals, laterals, and cuspids in order from the midline to the posterior. The posterior teeth, from anterior to posterior, are first and second premolars; first, second, and third molars. Individual teeth are described according to their surfaces. The distal surface is towards the back of the mouth and the mesial is the surface towards the front of the mouth. The lingual or palatal surface is on the tongue side of the teeth. The labial or buccal surface is on the cheek or lip side of the teeth. The occlusal surface is where the maxillary and mandibular teeth meet.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

New oral apparatuses and methods for mandibular jaw manipulation are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

Figure 4:
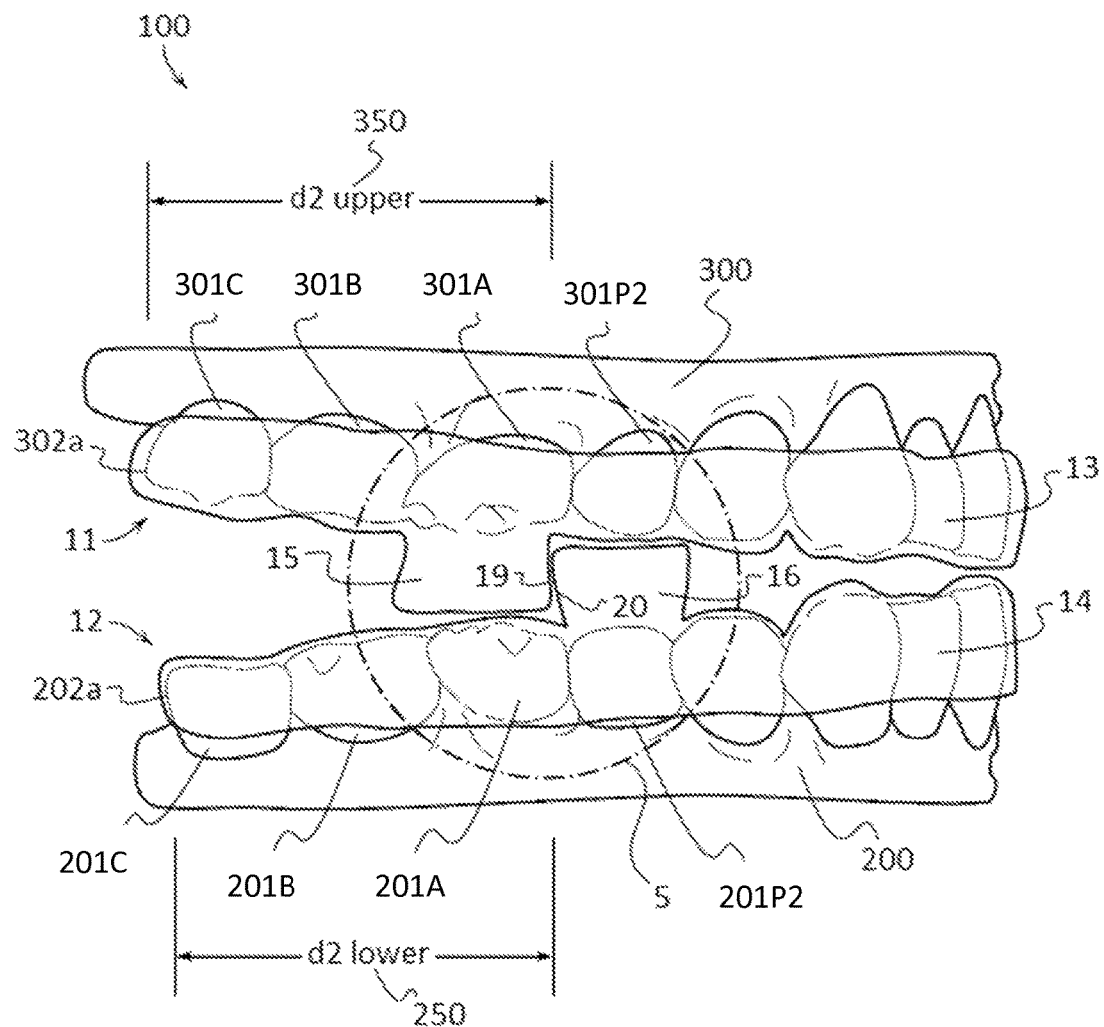
FIG. 4 depicts a side perspective view of an example of an oral apparatus with the upper element engaged to the maxillary teeth of the maxillary jaw and with the lower element engaged to the mandibular teeth of the mandibular jaw according to various embodiments described herein.

The present invention will now be described by example and through referencing the appended figures representing preferred and alternative embodiments. FIGS. 1 4 illustrate an example of an oral apparatus ("the apparatus") 100 according to various embodiments. In this example, the apparatus 100 comprises an upper element 11 with an upper tray 13 which is configured to engage one or more of the maxillary teeth, and a lower element 12 with a lower tray 14 which is configured to engage one or more of the mandibular teeth of a user.

An upper tray 13 may comprise a generally U-shaped arch with one or more tooth depressions which may extend into the upper tray 13. The shape of the arch preferably corresponds at least mainly to the maxillary dental arch of the user. Each tooth depression may be configured to receive one or more surfaces of a tooth such as the distal surface, mesial surface, palatal surface, the buccal surface, and/or the occlusal surface. The tooth depressions are at least sufficiently wide and deep to be able to snuggly or frictionally fit the teeth of the patient at least for the mainly visible parts, thereby allowing the upper tray 13 to engage or secure to one or more maxillary teeth when portions of the maxillary teeth are received in the tooth depressions.

The upper element 11 may also comprise two upper anchor members 15, with a first upper anchor member 15 coupled to a first side of the upper tray 13 which is configured to engage the occlusal surface of one or more posterior maxillary teeth on a first side of the mouth and a second upper anchor member 15 coupled to a second side of the upper tray 13 above the portion of the upper tray 13 which is configured to engage the occlusal surface of one or more posterior maxillary teeth on a second side of the mouth.

An upper anchor member 15 may be configured as a protrusion which extends away from the upper tray 13 and therefore extends away from the occlusal surfaces of the maxillary teeth to which the upper tray 13 may be engaged to. In some embodiments, an upper tray 13 may comprise two upper anchor members 15, with a first upper anchor member 15 and a second upper anchor member 15 coupled to opposite sides of the upper tray 13. For example and in some embodiments, a first upper anchor member 15 may be coupled to the upper tray 13 so that when the upper tray 13 is engaged to the maxillary teeth, the first upper anchor member 15 may be positioned generally over the first maxillary molars such as the maxillary first molar 301A (FIG. 4) and in some instances also over the maxillary second molar 301B (FIG. 4) (second and third from the rear on FIG. 1) on a first side of the mouth while a second upper anchor member 15 may be coupled to the upper tray 13 so that when the upper tray 13 is engaged to the maxillary teeth, the second upper anchor member 15 may be positioned generally over the first maxillary molars such as the maxillary first molar 301A (FIG. 4) and in some instances also over the maxillary second molar 301B (FIG. 4) (second and third from the rear on FIG. 1) on a second side of the mouth.

In other embodiments, one or more upper anchor members 15 may be coupled to anywhere along the upper tray 13 and preferably coupled so that an upper anchor member 15 on a first side of the upper tray 13 may generally mirror the positioning of an upper anchor member 15 on a second side of the upper tray 13.

Each upper anchor member 15 may comprise an upper bite plane 17 which may form the portion of the upper tray 13 that extends farthest from the occlusal surfaces of the maxillary teeth when the upper tray 13 is be engaged to the maxillary teeth. Additionally, each upper anchor member 15 may comprise an upper contact surface 19 which may generally form the mesial surface of the upper anchor member 15 and extend from the upper bite plane 17 to the upper tray 13.

Figure 5:
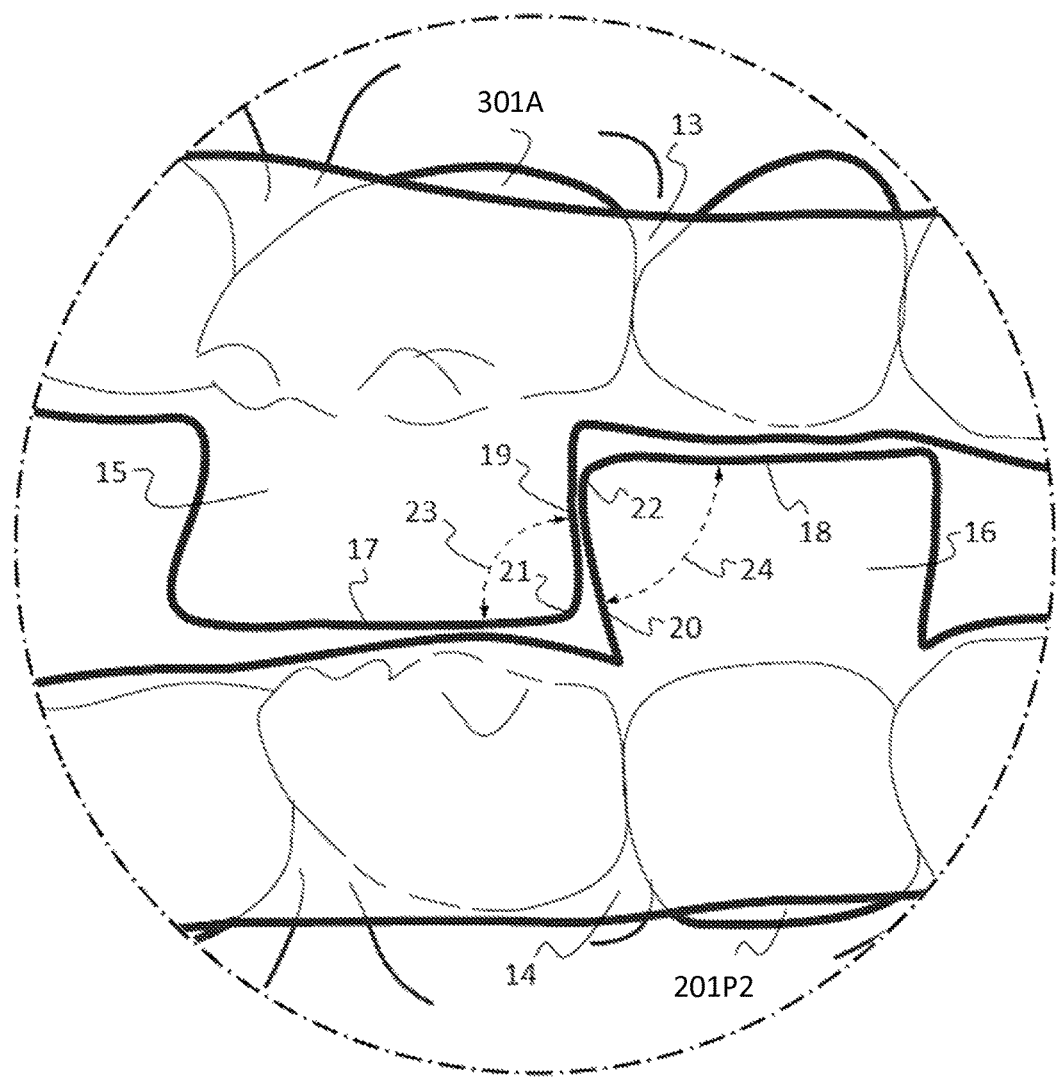
FIG. 5 illustrates an enlarged view of a portion of the example of an oral apparatus with the upper element engaged to the maxillary teeth of the maxillary jaw and with the lower element engaged to the mandibular teeth of the mandibular jaw depicted in FIG. 5 according to various embodiments described herein.

In some embodiments, the upper bite plane 17 and the upper contact surface 19 may each comprise a generally planar shape with the upper bite plane 17 disposed substantially parallel to the occlusal surfaces of the maxillary teeth when the upper tray 13 is be engaged to the maxillary teeth. In other embodiments, an upper bite plane 17 and/or an upper contact surface 19 may comprise a concave, convex, or any other shape including combinations of shapes. Portions of the upper contact surface 19 farthest from the upper bite plane 17 may be angled towards the upper bite plane 17 so that the upper contact surface 19 may be coupled to the upper bite plane 17 at upper medial corner 21 with upper anchor member corner angle 23 that is between 45 and 135 degrees. In further embodiments and as shown in FIGS. 4 and 5, an upper anchor member 15 may comprise a shape such as a block which generally resembles an acute trapezoid prism with the portion of the upper contact surface 19 farthest from the upper bite plane 17 acutely angled towards the upper bite plane 17 and the upper bite plane 17 forming the longer base edge of the acute trapezoid. In alternative embodiments, an upper anchor member 15 may be configured with the shape of a rectangular prism, cuboid prism, or any other shape including combinations of shapes.

A lower tray 14 may comprise a generally U-shaped arch with one or more tooth depressions which may extend into the lower tray 14. The shape of the arch preferably corresponds at least mainly to the mandibular dental arch of the user. Each tooth depression may be configured to receive one or more surfaces of a tooth such as the distal surface, mesial surface, palatal surface, the buccal surface, and/or the occlusal surface. The tooth depressions are at least sufficiently wide and deep to be able to snuggly or frictionally fit the teeth of the patient at least for the mainly visible parts, thereby allowing the lower tray 14 to engage or secure to one or more mandibular teeth when portions of the mandibular teeth are received in the tooth depressions.

The lower element 12 may also comprise two lower anchor members 16, with a first lower anchor member 16 coupled to a first side of the lower tray 14 which is configured to engage the occlusal surface of one or more posterior mandibular teeth on a first side of the mouth and a second lower anchor member 16 coupled to a second side of the lower tray 14 above the portion of the lower tray 14 which is configured to engage the occlusal surface of one or more posterior mandibular teeth on a second side of the mouth.

A lower anchor member 16 may be configured as a protrusion which extends away from the lower tray 14 and therefore extends away from the occlusal surfaces of the mandibular teeth to which the lower tray 14 may be engaged to. In some embodiments, a lower tray 14 may comprise two lower anchor members 16, with a first lower anchor member 16 and a second lower anchor member 16 coupled to opposite sides of the lower tray 14. For example and in some embodiments, a first lower anchor member 16 may be coupled to the lower tray 14 so that when the lower tray 14 is engaged to the mandibular teeth 201, the first lower anchor member 16 may be positioned generally over the mandibular second premolar 201P2 and in some instances the mandibular first molar 201A (second and third from the rear on FIG. 1) on a first side of the mouth while a second lower anchor member 16 may be coupled to the lower tray 14 so that when the lower tray 14 is engaged to the mandibular teeth, the second lower anchor member 16 may be positioned generally over the mandibular second premolar 201P2 and in some instances the mandibular first molar 201A (second and third from the rear on FIG. 1) on a second side of the mouth. In other embodiments, one or more lower anchor members 16 may be coupled to anywhere along the lower tray 14 and preferably coupled so that a lower anchor member 16 on a first side of the lower tray 14 may generally mirror the positioning of a lower anchor member 16 on a second side of the lower tray 14.

Each lower anchor member 16 may comprise a lower bite plane 18 which may form the portion of the lower tray 14 that extends farthest from the occlusal surfaces of the mandibular teeth when the lower tray 14 is be engaged to the mandibular teeth. Additionally, each lower anchor member 16 may comprise a lower contact surface 20 which may generally form the distal surface of the lower anchor member 16 and extend from the lower bite plane 18 to the lower tray 14.

In some embodiments, the lower bite plane 18 and the lower contact surface 20 may each comprise a generally planar shape with the lower bite plane 18 disposed substantially parallel to the occlusal surfaces of the mandibular teeth when the lower tray 14 is be engaged to the mandibular teeth. In other embodiments, a lower bite plane 18 and/or a lower contact surface 20 may comprise a concave, convex, or any other shape including combinations of shapes. Portions of the lower contact surface 20 farthest from the lower bite plane 18 may be angled towards the lower bite plane 18 so that the lower contact surface 20 may be coupled to the lower bite plane 18 at lower medial corner 22 with a lower member corner angle 24 that is between 45 and 135 degrees. In further embodiments and as shown in FIGS. 4 and 5, a lower anchor member 16 may comprise a shape which generally resembles an acute trapezoid prism with the portion of the lower contact surface 20 farthest from the lower bite plane 18 acutely angled towards the lower bite plane 18 and the lower bite plane 18 forming the longer base edge of the acute trapezoid. In alternative embodiments, a lower anchor member 16 may be configured with the shape of a rectangular prism, cuboid prism, or any other shape including combinations of shapes.

As perhaps best shown in FIG. 4, a lower element 12 may comprise a lower anchor member 16 coupled to the lower tray 14 and the upper element 11 may comprise an upper anchor member 15 coupled to the upper tray 13 with one or more portions of the upper anchor member 15 configured to contact one or more portions of the lower element 11 and one or more portions of the lower anchor member 16 configured to contact one or more portions of the upper element 12.

In some embodiments, the upper contact surface 19 of a first and a second upper anchor member 15 may be configured to contact a portion of the lower contact surface 20 of a first and a second lower anchor member 16 while the upper element 11 is engaged to the maxillary jaw, the lower element 12 is engaged to the mandibular jaw, and the mouth is in a closed position. The upper contact surface 19 of the first upper anchor member 15 may be configured to contact a portion of the lower contact surface 20 of the first lower anchor member 16 and the upper contact surface 19 of the second upper anchor member 15 may be configured to contact a portion of the lower contact surface 20 of the second lower anchor member 16 while the upper element 11 is engaged to the maxillary jaw, the lower element 12 is engaged to the mandibular jaw, and the mouth is in a closed position. Generally, a closed position may be defined when the upper element 11 which is engaged to the maxillary jaw and the lower element 12 which is engaged to the mandibular jaw are in proximity to each other, such as when portions of the upper element 11 and lower element 12 are contacting each other.

In further embodiments, the upper bite plane 17 may be configured to contact a portion of a lower tray 14 and/or the lower bite plane 18 may be configured to contact a portion of an upper tray 13. The upper contact surface 19 may extend from the upper tray 13 to intersect with the upper bite plane 17 at an upper medial corner 21 to form upper anchor member corner angle 23. Upper anchor member corner angle 23 may comprise any angle, such as between 45 and 135 degrees. The lower contact surface 20 may extend from the lower tray 14 to intersect with the lower bite plane 18 at a lower medial corner 22 to form lower member corner angle 24. Lower member corner angle 24 may comprise any angle, such as between 45 and 135 degrees.

In some embodiments, the upper contact surface 19 of the first and second upper anchor members 15 may be oriented at a complementary angle to the lower contact surface 20 of the first and second lower anchor members 16. The upper contact surface 19 of the first upper anchor member 15 may be oriented at a complementary angle to the lower contact surface 20 of the first lower anchor member 16 while the upper contact surface 19 of the second upper anchor member 15 may be oriented at a complementary angle to the lower contact surface 20 of the second lower anchor member 16. Orienting the upper contact surface 19 of an upper anchor member 15 to the lower contact surface 20 of a lower anchor member 16 with a complementary angle may be accomplished when the upper anchor member corner angle 23 is complementary to the lower member corner angle 24 thereby allowing the surface area contact between the upper contact surface 19 and the lower contact surface 20 to be maximized. In further embodiments, the upper anchor member corner angle 23 may be between 45 to 135 degrees and the lower member corner angle 24 may be between 45 to 135 degrees. In still further embodiments, the upper anchor member corner angle 23 may be between 45 to 135 degrees and complementary to the lower member corner angle 24 which may be between 45 to 135 degrees. In further embodiments, the upper anchor member corner angle 23 may be less than 90 degrees and the lower member corner angle 24 may be less than 90 degrees. In still further embodiments, the upper anchor member corner angle 23 may be less than 90 degrees and complementary to the lower member corner angle 24 which may be less than 90 degrees.

Figure 8:
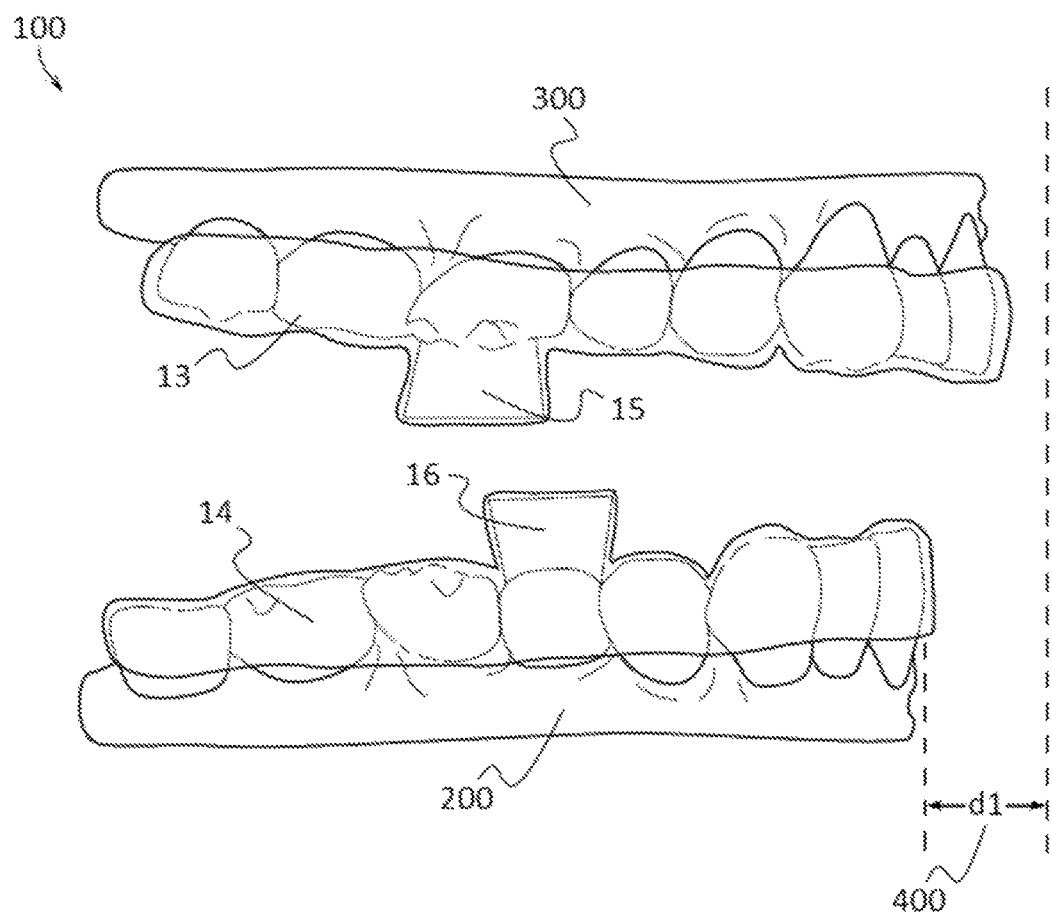
FIG. 8 illustrates a side perspective view of an example of an oral apparatus with the upper element engaged to the maxillary teeth of the maxillary jaw and with the lower element engaged to the mandibular teeth of the mandibular jaw and the progressive advancement distance to align the mandibular jaw and maxillary jaw according to various embodiments described herein.

The oral apparatuses 100 and methods for mandibular jaw manipulation disclosed herein may be used to maintain or increase a mandibular advancement distance, thereby adjusting the positional relationship between a mandible and maxilla of a mouth. The mandibular advancement distance describes the dental practitioner selected distance that the mandibular jaw is to be moved relative to the maxillary jaw towards the anterior of the mouth. In some embodiments and as shown in FIG. 8, the mandibular advancement distance may be broken up into a series of progressive advancement distances (d1) 400 to decrease the stress on a patient which can be caused by moving the mandible a large mandibular advancement distance relative to the maxilla of a mouth. A user may wear two or more, such as a series, of oral apparatuses 100 with progressively increasing progressive advancement distances (d1) 400 until the progressive advancement distance (d1) 400 of an apparatus 100 is equal to the selected mandibular advancement distance. For example, if the selected mandibular advancement distance is three millimeters for a patient, the patient may first wear an apparatus 100 with a progressive advancement distance (d1) 400 of one millimeters for a period of time, then wear an apparatus 100 with a progressive advancement distance (d1) 400 of two millimeters for a period of time, and finally wear an apparatus 100 with a progressive advancement distance (d1) 400 of three millimeters for a period of time thereby effectively moving the advancement of the mandibular in 1 mm increments as is currently a requirement for an oral appliance used in obstructive sleep Apnea.

As shown in FIG. 4, a first upper anchor member 15 may be configured to contact a first lower anchor member 16 and a second upper anchor member 15 is configured to contact a second lower anchor member 16 to adjust the positional relationship between the mandible and the maxilla of a mouth. Each upper anchor member 15 may be positioned on the upper element 11 at an upper anchor member distance (d2 upper) 350 which is the distance between a position in the posterior of the mouth, such as the farthest posterior maxillary molar 302 or the distal surface of farthest posterior maxillary molar 302a, and the upper anchor member 15. Similarly, each lower anchor member 16 may be positioned on the lower element 12 at a lower member distance (d2 lower) 250 which is the distance between a position in the posterior of the mouth, such as the farthest posterior mandibular molar 202 or the distal surface of farthest posterior mandibular molar 202a, and the lower anchor member 16. In some embodiments, d2 lower 250 or d2 upper 350 may be generally equal to a progressive advancement distance (d1) 400 (FIG. 8). In other embodiments, d2 lower 250 and d2 upper 350 may both generally add up to the progressive advancement distance (d1) 400. In further embodiments, the d2 upper 350 of an upper anchor member 15 may be greater than, equal to, or less than the d2 lower 250 of a lower anchor member 16.

It is important to note that d2 is a relative distance in that increasing the d2 upper 350 of a first upper anchor member 15 and/or a d2 lower 250 of a first lower anchor member 16 will increase the mandibular advancement distance when the first upper anchor member 15 and first lower anchor member 16 contact each other when the mouth is in a closed position. Conversely, decreasing the d2 upper 350 of a first upper anchor member 15 and/or a d2 lower 250 of a first lower anchor member 16 will decrease the mandibular advancement distance when the first upper anchor member 15 and first lower anchor member 16 contact each other when the mouth is in a closed position. Also in this manner, increasing the d2 upper 350 of a first upper anchor member 15 and/or a d2 lower 250 of a first lower anchor member 16 will increase the progressive advancement distance (d1) 400, while decreasing the d2 upper 350 of a first upper anchor member 15 and/or a d2 lower 250 of a first lower anchor member 16 will decrease the progressive advancement distance (d1) 400 when the first upper anchor member 15 and first lower anchor member 16 contact each other when the mouth is in a closed position.

When the upper element 11 is engaged to the maxillary teeth and the lower element 12 is engaged to the mandibular teeth, the upper contact surface 19 of an upper anchor member 15 on a first side of the mouth is configured to contact the lower contact surface 20 of a lower anchor member 16 on a first side of the mouth. Similarly, the upper contact surface 19 of an upper anchor member 15 on a second side of the mouth is configured to contact the lower contact surface 20 of a lower anchor member 16 on the second side of the mouth. Preferably, a first lower anchor member 16 and second lower anchor member 16 may be coupled to opposing sides of the lower tray 14 in a generally mirrored configuration so that the first lower anchor member 16 may be positioned over approximately the same tooth or teeth on a first side of the mouth as the tooth or teeth the second lower anchor member 16 may be positioned over on a second side of the mouth. As the two upper elements 11 and lower elements 12 are brought together, such as when a user brings their jaws together, the upper contact surfaces 19 may be positioned to contact lower contact surfaces 20 thereby directing the lower jaw and mandibular teeth in a mesial direction relative to the upper jaw and maxillary teeth. In further embodiments, the movement of the upper element 11 towards the lower element 12, and therefore the movement of the mandibular jaw towards the maxillary jaw, such as when the user closes their mouth, may be arrested when a portion of the lower bite planes 18 contact a portion of the upper tray 13 and/or when a portion of the upper bite planes 17 contact a portion of the lower tray 14.

In some embodiments, the upper tray 13 may be configured to engage one or more maxillary teeth and the lower tray 14 may be configured to engage one or more mandibular teeth, and as the upper element 11 and lower element 12 are brought together the upper contact surfaces 19 may be positioned to contact lower contact surfaces 20 thereby directing the lower jaw in a mesial direction relative to the upper jaw for mandibular advancement purposes such as to address a snoring condition of the user. For example, the therapeutic position of the lower jaw relative to the upper jaw to address a snoring problem may be recorded clinically, such as a six millimeter advancement of the mandibular jaw relative to the maxillary jaw. Two upper anchor members 15 may be positioned on opposite sides of the upper element 11, each with a d2 upper 350, and two lower anchor members 16 may be positioned on opposite sides of the lower element 12, each with a d2 lower 250. The d2 upper 350 of each upper anchor member 15 and the d2 lower 250 of each lower anchor member 16, may be selected so that when a first upper anchor member 15 contacts a first lower anchor member 16 and a second upper anchor member 15 contacts a second lower member 16 when the mouth is in a closed position, the mandibular jaw may be advanced approximately six millimeters.

In some embodiments, the upper tray 13 may be configured to engage one or more maxillary teeth and the lower tray 14 may be configured to engage one or more mandibular teeth, and as the upper element 11 and lower element 12 are brought together the upper contact surfaces 19 may be positioned to contact lower contact surfaces 20 thereby directing the lower jaw in a mesial direction relative to the upper jaw for mandibular advancement purposes such as to address a snoring condition of the user. Additionally, the upper tray 13 may also be configured to engage one or more maxillary teeth for orthodontic purposes such as to move one or more maxillary teeth and/or the lower tray 14 may be configured to engage one or more mandibular teeth for orthodontic purposes such as to move one or more mandibular teeth of the user. For example, the anchor members 15, 16, may be positioned for a selected mandibular advancement distance to alleviate snoring, while the upper tray 13 and/or lower tray 14 may be configured to engage one or more teeth in an orthodontic manner to move the one or more teeth while the user is wearing the apparatus 100 and the mouth is in a closed position.

Figure 6:
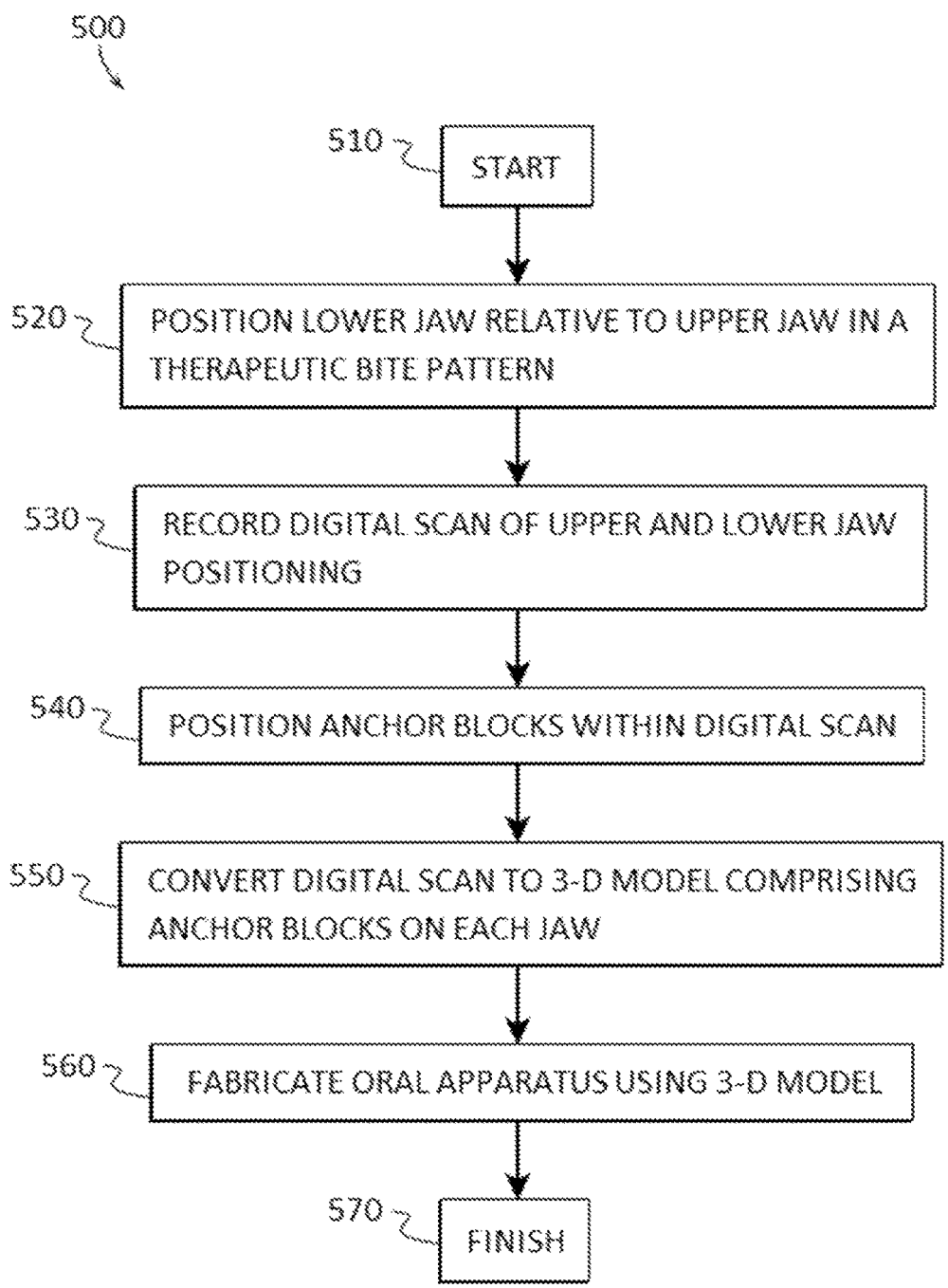
FIG. 6 shows a flow chart of a method for forming an oral apparatus according to various embodiments described herein.

FIG. 6 illustrates a flow chart of a method for forming an oral apparatus ("the method") 500 according to various embodiments described herein. In some embodiments, the method 500 may be used to form an oral apparatus for therapeutic mandibular advancement such as when a patient or user presents with SDB (sleep disorder Breathing) which may include Snoring and Sleep Apnea, OSA (obstructive Sleep Apnea) which are typically determined through a Sleep test and optionally to orthodontically move one or more teeth. The method 500 may start 510 and the lower (mandibular) jaw may be positioned relative to the upper (maxillary) jaw in a therapeutic bite pattern for a user in step 520. In some embodiments, the therapeutic bite pattern may position the lower jaw relative to the upper jaw a required distance in order to address the condition of the user. In further embodiments, a sleep Physician may make the diagnosis and dispense a prescription for an oral apparatus for snoring or the treatment of Sleep Apnea to a dentist versed in Dental Sleep Medicine comprising a required distance to advance the lower jaw relative to the upper jaw.

In step 530, a digital scan of upper and lower jaw positioning may be recorded. The positioning may include positioning data which describes the therapeutic bite pattern and the dental arches of the user. In some embodiments, the positioning data may be recorded by a digital intraoral impression scanner such as an iTero® Intraoral scanner or the like. In further embodiments, the positioning data may be recorded as a STL (STereoLithography) file format such as is native to the stereolithography CAD software created by 3D Systems. In other embodiments, the positioning data may be recorded in any file format which may describe the surface geometry of a three-dimensional object, such as the upper and lower jaw positioning to achieve the therapeutic bite pattern.

In step 540, one or more anchor members 15, 16, (FIGS. 1-4) may be positioned within the digital scan. In some embodiments, one or more anchor members 15, 16, may be positioned within the digital scan by importing the digital scan into a 3-D scanning reverse engineering software program such as Orchestrate Orthodontic Technologies® scanning reverse engineering software. Using the software program, one or more upper anchor members 15 may be positioned proximate to one or more maxillary teeth 301 on one or more sides of the upper or maxillary jaw 300, with each upper anchor member 15 comprising a d2 upper 350 (FIG. 4). Also using the software program, one or more lower anchor members 16 may be positioned proximate to one or more mandibular teeth 201 on one or more sides of the lower or mandibular jaw 200, with each lower anchor member 16 comprising a d2 lower 250 (FIG. 4). The positioning of the anchor members 15, 16, may be selected so that the upper contact surface 19 of an upper anchor member 15 on a first side of the mouth is configured to contact the lower contact surface 20 of a lower anchor member 16 on a first side of the mouth. Similarly, the upper contact surface 19 of an upper anchor member 15 on a second side of the mouth is configured to contact the lower contact surface 20 of a lower anchor member 16 on the second side of the mouth. Preferably, a first lower anchor member 16 and second lower anchor member 16 may be coupled to opposing sides of the lower tray 14 in a generally mirrored configuration so that the first lower anchor member 16 may be positioned over approximately the same tooth or teeth on a first side of the mouth as the tooth or teeth the second lower anchor member 16 may be positioned over on a second side of the mouth. As the upper anchor members 15 and lower anchor members 16 are brought together, such as when a user brings their jaws together in a closed position, the four contact surfaces 19, 20, may contact each other thereby directing the lower jaw and mandibular teeth in a mesial direction relative to the upper jaw and maxillary teeth. In addition to the selectable positioning of the anchor members 15,16, the size and dimension of each anchor member 15,16 may be adjusted and personalized for each patient. By way of non-limiting example, a sleep patient suffering from jaw muscle soreness may call for reduced vertical dimensions of each anchor member 15,16 (i.e. the distance between the bite planes 17,18 of the anchor members 15,16 and the trays 13,14) while a patient suffering from excessive snoring may call for an increase in vertical dimensions of each anchor member 15,16 (i.e. the distance between the bite planes 17,18 of the anchor members 15,16 and the trays 13,14).

Next in step 550, the digital scan with positioned anchor members 15, 16, may be converted to a 3-D model comprising one or more anchor members 15, 16, on each jaw. The 3-D model may comprise one or more upper anchor members 15 positioned proximate to one or more maxillary teeth on one or more sides of the upper jaw, and one or more lower anchor members 16 positioned proximate to one or more mandibular teeth on one or more sides of the lower jaw. In some embodiments, the digital scan with positioned anchor members 15, 16, may be converted to a 3-D model with additive manufacturing, such as with Three-dimensional printing or 3D printing. In further embodiments, the 3-D model may comprise one or more anchor members 15, 16, positioned on a three dimensional model of each jaw. In yet further embodiments, the digital scan 550 with anchor members 15,16 may be used as a digital image file to be used by a mill or otherwise fabricate the apparatus 100 directly using the digital rendered image file without fabricating a 3-D model (i.e. bypassing part of step 560) with said apparatus 100 being then worn by a patient.

In some embodiments, an oral apparatus 100 may be first be fabricated first using the 3-D model (step 560) which comprises one or more upper anchor members 15 positioned proximate to one or more maxillary teeth on one or more sides of the upper jaw, and one or more lower anchor members 16 positioned proximate to one or more mandibular teeth on one or more sides of the lower jaw. In some embodiments, the apparatus 100 may be fabricated by thermal-forming a suitable oral plastic, such as Biocryl® or any other dental splint material, over the each jaw of the 3-D model. Once formed over the 3-D model, portions of the thermal formed material which are molded around the mandibular teeth of the 3-D model, thereby forming depressions to receive the mandibular teeth of the user may also form the lower tray 14, while portions of the thermal formed material which are molded around the anchor members of the 3-D model lower jaw may form the lower anchor members 16 coupled to the lower tray 14. Similarly, once formed over the 3-D model, portions of the thermal formed material which are molded around the maxillary teeth of the 3-D model, thereby forming depressions to receive the maxillary teeth of the user may also form the upper tray 13, while portions of the thermal formed material which are molded around the anchor members of the 3-D model upper jaw may form the upper anchor members 15 coupled to the upper tray 13. In still further embodiments, the fabrication of step 560 may include final or routine adjustments by the dental practitioner to ensure a proper and comfortable fit for the user. After step 560, the method 500 may finish 570.

Figure 7:
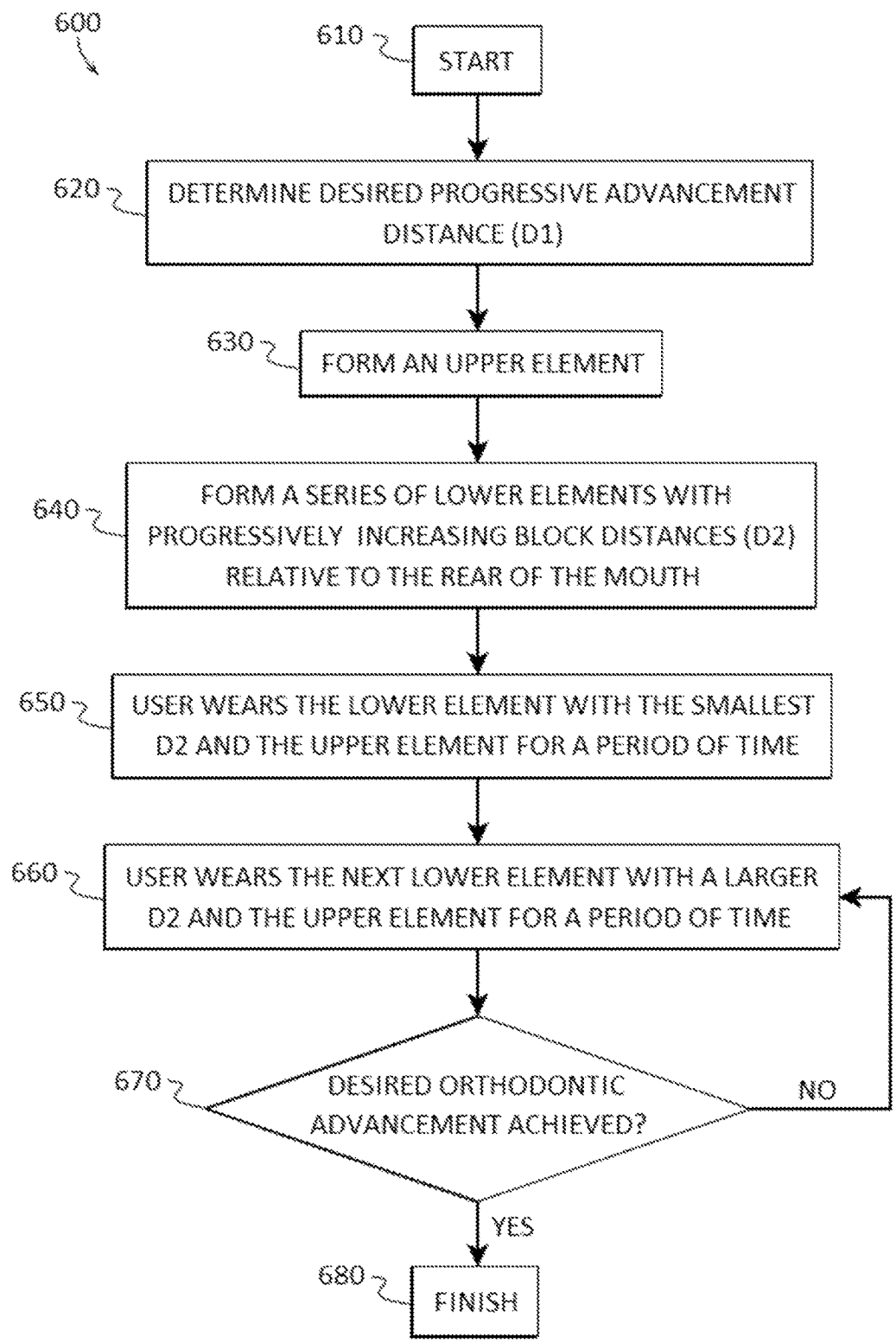
FIG. 7 depicts a flow chart of a method for performing a progressive mandibular jaw advancement according to various embodiments described herein.

FIG. 7 illustrates a flow chart of a method for performing a progressive mandibular jaw advancement ("the method") 600 according to various embodiments described herein. In some embodiments, the method 600 may be used to progressively achieve a therapeutic mandibular advancement such as when a patient or user presents with SDB (sleep disorder Breathing) which may include Snoring and Sleep Apnea, OSA (obstructive Sleep Apnea) which are typically determined through a Sleep test and optionally to orthodontically move one or more teeth. The therapeutic mandibular advancement may be divided into any number of increments to produce a desired progressive mandibular advancement distance (d1) 400. In this embodiment, the upper anchor members 15 remain in position proximate to the maxillary molars, while the lower anchor members 16 are positioned proximate to different mandibular molars relative to the different lower elements 12 in a series of lower elements 12. In alternative embodiments, the lower anchor members 16 may remain in position proximate to the mandibular molars, while the upper anchor members 15 may be positioned proximate to different maxillary molars relative to the different upper elements 11 in a series of upper elements 11. In further alternative embodiments, the upper anchor members 15 may be positioned proximate to different maxillary molars relative to the different upper elements 11 in a series of upper elements 11 and the lower anchor members 16 are positioned proximate to different mandibular molars relative to the different lower elements 12 in a series of lower elements 12 so that the user or patient may wear a series of lower elements 12 and a series of upper elements 11 in order to achieve mandibular advancement.

The method 600 may start 610 and the desired progressive mandibular advancement distance (d1) 400 may be determined or selected for the patient in which the lower (mandibular) jaw may be positioned relative to the upper (maxillary) jaw in a therapeutic bite pattern for a patient in step 620. As shown in FIG. 8, the progressive mandibular advancement distance (d1) 400 may be described as the distance the lower jaw 200 is to be advanced forward to allow the alignment of the teeth of the upper jaw 300 with the lower jaw 200 to produce a therapeutic bite pattern. In some embodiments, the desired progressive mandibular advancement distance (d1) 400 may produce a therapeutic bite pattern which may position the lower jaw 200 relative to the upper jaw 300 a required distance in order to address the condition of the user. In further embodiments, a sleep Physician may make the diagnosis and dispense a prescription for an oral apparatus for snoring or the treatment of Sleep Apnea to a dentist versed in Dental Sleep Medicine comprising a required distance to advance the lower jaw relative to the upper jaw.

In step 630, an upper element 11 may be formed. The upper element 11 may comprise a first upper anchor member 15 and a second upper anchor member 15 coupled to the upper tray 13 to be positioned proximate to one or more of the maxillary molar teeth. The upper element 11 may be optionally formed according to the method 500 of described in FIG. 6.

In step 640, a series of lower elements 12 with progressively increasing lower member distance (d2 lower) 250 (FIG. 4) may be formed. The lower element 12 may comprise a first lower anchor member 16 and a second lower anchor member 16 coupled to the lower tray 14 to be positioned proximate to one or more of the mandibular molar teeth. In some embodiments, a series of lower elements 12 may comprise two or more lower elements 12, each with progressively increasing d2 lower 250 relative to another lower element 12, with at least one lower element 12 of the series comprising a d2 lower 250 generally equal to the desired progressive mandibular advancement distance (d1) 400 (FIG. 8). For example, the selected mandibular advancement distance for a patient may be six millimeters. The therapeutic mandibular advancement may be divided into three increments to produce a desired progressive mandibular advancement distance (d1) 400 of two millimeters. In this example, the series of lower elements 12 may comprise three lower elements 12, with the first lower element 12, comprising a d2 lower 250 of two millimeters, the second lower element 12, comprising a d2 lower 250 of four millimeters, and the third lower element 12, comprising a d2 lower 250 of six millimeters. In further embodiments, any desired progressive advancement distance (d1) 400 may be used and any number of lower elements 12, each with any desired d2 lower 250 may be used.

Next, in step 650 the user or patient may wear the upper element 11 and the lower element 12 with the smallest d2 lower 250 (FIG. 4) for a period of time. Using the current example, the user may wear the upper element 11 and the lower element 12 with the smallest d2 lower 250 of two millimeters for a period of time. The period of time may be selected by the practitioner. A first upper anchor member 15 may be configured to contact a first lower anchor member 16 and a second upper anchor member 15 may be configured to contact a second lower anchor member 16 to adjust the positional relationship between the mandible 200 and the maxilla 300 of a mouth to a distance equal to the therapeutic mandibular advancement when the mouth is in a closed position.

Next, in step 660 the user or patient may wear the upper element 11 and the lower element 12 with a d2 lower 250 (FIG. 4) that is larger than the d2 lower 250 of the previously worn lower element 12 for a period of time. Using the current example, the user may wear the upper element 11 and the lower element 12 with the d2 lower 250 of four millimeters for a period of time. The period of time may be selected by the practitioner.

In decision block 670, the practitioner may determine if the desired therapeutic mandibular advancement has been achieved. If the desired therapeutic mandibular advancement has not been achieved, the method 600 may proceed to step 660 and the user or patient may wear the upper element 11 and the lower element 12 with a d2 lower 250 that is larger than d2 lower 250 of the previously worn lower element 12 for a period of time. Using the current example, the user may wear the upper element 11 and the lower element 12 with the d2 lower 250 of six millimeters for a period of time. The period of time may be selected by the practitioner.

Once the desired therapeutic mandibular advancement has been achieved, such as when the d2 lower 250 FIG. 4) is generally equal to the desired therapeutic mandibular advancement and/or the progressive advancement distance (d1) 400 (FIG. 8), the method 600 may finish 680.

While some materials have been provided, in other embodiments, the elements that comprise the apparatus 100 such as the upper element 11, lower element 12, upper tray 13, lower tray 14, upper anchor member 15, and lower anchor member 16 may be made from durable dental safe materials such as metals and metal alloys, hard plastics, fiber reinforced plastics, carbon fiber, resins, polymers or any other suitable materials including combinations of materials. Additionally, one or more elements may be made from or comprise durable and slightly flexible dental safe materials such as soft plastics, silicone, soft rubbers, or any other suitable materials including combinations of materials. In some embodiments, one or more of the elements that comprise the apparatus 100 may be coupled or connected together with heat bonding, chemical bonding, adhesives, clip type fasteners, rivet type fasteners, threaded type fasteners, other types of fasteners, or any other suitable joining method. In other embodiments, one or more of the elements that comprise the apparatus 100 may be coupled or removably connected by being press fit or snap fit together, by one or more fasteners such as threaded type fasteners, sealable tongue and groove fasteners, snap fasteners, clip type fasteners, a push-to-lock type connection method, a turn-to-lock type connection method, slide-to-lock type connection method or any other suitable temporary connection method as one reasonably skilled in the art could envision to serve the same function. In further embodiments, one or more of the elements that comprise the apparatus 100 may be coupled by being one of connected to and integrally formed with another element of the apparatus 100. In yet further embodiments, one or more of the elements that comprise the apparatus 100 may comprise retention depressions or protrusions which can be added using dental instruments or by adding composite to the apparatus 100 to improve retention of the apparatus to the teeth as needed.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An apparatus for adjusting the positional relationship between a mandible and maxilla of a mouth, the apparatus comprising:

an upper tray configured to receive a plurality of maxillary teeth with said upper tray having;
  i. a first upper anchor member protruding below a first side of the upper tray, the first upper anchor member having a first upper bite plane extending along a lower distal edge of the first upper anchor member, a first upper contact surface extending along an anterior side edge of the first upper anchor member, and a first upper medial corner connecting the first upper bite plane to the first upper contact surface;
  ii. a second upper anchor member protruding below a second side of the upper tray, the second upper anchor member having a second upper bite plane extending along a lower distal edge of the second upper anchor member, a second upper contact surface extending along an anterior side edge of the second upper anchor member, and a second upper medial corner connecting the second upper bite plane to the second upper contact surface;

a lower tray configured to receive a plurality of mandibular teeth with said lower tray having;
  i. a first lower anchor member protruding above and integrally formed to a first side of the lower tray but not protruding upwardly past the upper tray when the mandible and the maxilla of the mouth are in a closed position; the first lower anchor member having a first lower bite plane extending along an upper distal edge of the first lower anchor member and configured to make contact with an underside of the upper tray at a location adjacent to but not above the first upper anchor member, a first continuous lower contact surface extending along a posterior side edge of the first lower anchor member starting at and in contact with the lower tray, the first continuous lower contact surface having an upwardly posterior slope, the first continuous lower contact surface further configured to maximize surface area engagement of the first upper contact surface of the first upper anchor member, the first lower anchor member further comprising a first lower medial corner having a first lower corner angle connecting the first lower bite plane to the first continuous lower contact surface, the first lower corner angle being less than 90 degrees and the first lower medial corner being located at a position below the upper tray and above the lower tray when the mandible and the maxilla of the mouth are in the closed position;

ii. a second lower anchor member protruding above and integrally formed to a second side of the lower tray but not protruding upwardly past the upper tray when the mandible and the maxilla of the mouth are in the closed position; the second lower anchor member having a second lower bite plane extending along an upper distal edge of the second lower anchor member and configured to make contact with an underside of the upper tray at a location adjacent to but not above the second upper anchor member, a second continuous lower contact surface extending along a posterior side edge of the second lower anchor member starting at and in contact with the lower tray, and having an upwardly posterior slope, the second continuous lower contact surface configured to maximize surface area engagement of the second upper contact surface of the second upper anchor member and the second upper anchor member further comprising a second lower medial corner having a second lower corner angle connecting the second lower bite plane to the second continuous lower contact surface, the second lower corner angle being less than 90 degrees and the second lower medial corner being located at a position below the upper tray and above the lower tray when the mandible and the maxilla of the mouth are in the closed position;

iii. the first and second lower anchor members each having a first width at a portion distal to the lower tray and a second width at a portion proximal to the lower tray, the first width being wider than the second width and formed in-part by the continuous first and second contact surface; and wherein the first upper anchor member first upper contact surface is configured to contact a maximum surface area of first continuous lower contact surface of the first lower anchor member and the second upper anchor member second upper contact surface is configured to contact a maximum surface area of the second continuous lower contact surface of the second lower anchor member to increase frictional contact between the first and second continuous lower contact surfaces and to adjust the positional relationship between the mandible and the maxilla of the mouth thereby preventing the mandible from disengaging with the maxilla during sleep.

2. The apparatus of claim 1, wherein the first and second upper anchor members are positioned proximate to the maxillary molar teeth and configured to contact with the first and second lower anchor members positioned proximate to the mandibular second premolar teeth to cause the mandible to move forwards relative to the maxilla when the mouth is in a closed position and the upper anchor member is contacting the lower anchor member.

3. The apparatus of claim 1, wherein the first upper anchor member first upper medial corner has a first upper corner angle less than 90 degrees and the second upper anchor member second upper medial corner has a second upper corner angle less than 90 degrees.

4. The apparatus of claim 3 wherein the first upper contact surface of the first upper anchor member is oriented to contact and engage with the upwardly posterior sloped first lower contact surface of the first lower anchor member thereby preventing the mandible from disengaging with the maxilla during sleep.

\* \* \* \* \*